US012629081B2

(12) United States Patent
Hashimoto et al.

(10) Patent No.: US 12,629,081 B2
(45) Date of Patent: May 19, 2026

(54) RRI MEASUREMENT DEVICE, RRI MEASUREMENT METHOD AND RRI MEASUREMENT PROGRAM

(71) Applicant: NTT, Inc., Tokyo (JP)

(72) Inventors: Yuki Hashimoto, Tokyo (JP); Kei Kuwabara, Tokyo (JP); Nobuaki Matsuura, Tokyo (JP)

(73) Assignee: NTT, INC., Tokyo (JP)

( * ) Notice: Subject to any disclaimer, the term of this patent is extended or adjusted under 35 U.S.C. 154(b) by 435 days.

(21) Appl. No.: 18/247,818

(22) PCT Filed: Oct. 27, 2020

(86) PCT No.: PCT/JP2020/040192
§ 371 (c)(1),
(2) Date: Apr. 4, 2023

(87) PCT Pub. No.: WO2022/091195
PCT Pub. Date: May 5, 2022

(65) Prior Publication Data
US 2023/0397873 A1     Dec. 14, 2023

(51) Int. Cl.
*A61B 5/00*          (2006.01)
*A61B 5/308*        (2021.01)
*A61B 5/352*        (2021.01)
(52) U.S. Cl.
CPC .............. *A61B 5/352* (2021.01); *A61B 5/308* (2021.01)

(58) Field of Classification Search
CPC ...... A61B 5/352; A61B 5/308; A61B 5/02405
See application file for complete search history.

(56) References Cited

FOREIGN PATENT DOCUMENTS

| | | |
|---|---|---|
| JP | 08336502 A | 12/1996 |
| JP | 2015527173 A | 9/2015 |
| JP | 2016024495 A1 | 6/2017 |

OTHER PUBLICATIONS

Baba, et al., "A Scanning Method of Sensor Array for High-Speed Position Measurement," Collection of papers of the Society of Measurement and Automatic Control, vol. 33, No. 7, May 1997, pp. 588-596.
Elgendi et al., "Revisiting QRS Detection Methodologies for Portable, Wearable, Battery-Operated, and Wireless ECG Systems," PLOS One, www.plosone.org, Jan. 2014, vol. 9, Issue 1, pp. 1-18.

*Primary Examiner* — Scott M. Getzow
(74) *Attorney, Agent, or Firm* — Slater Matsil, LLP

(57)          ABSTRACT
An RRI measurement device includes: an R wave detection unit configured to detect a peak point of an R wave from a sampling data sequence of an electrocardiogram signal of a subject; an R wave detection unit configured to estimate a waveform near the R wave of the electrocardiogram signal on the basis of the peak point of the R wave detected by the R wave detection unit and sampling data of the electrocardiogram signal before and after the peak point and to detect the peak point of the R wave again on the basis of the estimated waveform; and an RRI calculation unit configured to calculate an RRI on the basis of time-series data of the peak point of the R wave detected by the R wave detection unit.

17 Claims, 7 Drawing Sheets

RRI MEASUREMENT DEVICE, RRI MEASUREMENT METHOD AND RRI MEASUREMENT PROGRAM

CROSS-REFERENCE TO RELATED APPLICATIONS

This application is a national phase entry of PCT Application No. PCT/JP2020/040192, filed on Oct. 27, 2020, which application is hereby incorporated herein by reference.

TECHNICAL FIELD

The present invention relates to an RRI measurement device, an RRI measurement method, and an RRI measurement program that detect an RRI that is an interval between two adjacent R waves from an electrocardiogram signal.

BACKGROUND

An R-R interval (RRI) in an electrocardiogram (ECG) is used for analysis of heart rate variability, diagnosis of arrhythmia, detection of heart disease and disorder of the automatic nerve system, and the like. With recent development of technology, real-time ECG acquisition and RRI detection have become possible by using a wearable device (see Non Patent Literature 1).

For example, there has been proposed an application that acquires time-series data of an ECG signal while clothes are worn by using a wearable device attached to the clothes, calculates a heart rate and an RRI on the basis of the ECG signal, and wirelessly transmits obtained data group to an external terminal such as a smartphone (see Patent Literature 1).

In general, accuracy of detecting an RRI from an ECG signal depends on a sampling rate of the ECG signal, and the analysis of the heart rate variability requires the sampling rate of 2 msec. or more, that is, 500 samples/sec. or more.

Meanwhile, in a case where signal acquisition is performed at the above high sampling rate in the wearable device, a calculation throughput increases and power consumption of the device increases, which are problematic.

CITATION LIST

Patent Literature

Patent Literature 1: JP 2016-24495 A

Non Patent Literature

Non Patent Literature 1: M. Elgandi et al., "Revisiting QRS Detection Methodologies for Portable, Wearable, Battery-Operated, and Wireless ECG Systems", PLOS ONE, Vol. 9, No. 1, e84018, 2014, DOI: 10.1371/journal. pone. 0084018.

SUMMARY

Technical Problem

Embodiments of the present invention have been made to solve the above problems, and an object of embodiments of the present invention is to provide an RRI measurement device, an RRI measurement method, and an RRI measurement program capable of accurately measuring an RRI of a subject on the basis of sampling data of an electrocardiogram signal acquired at a low sampling rate.

Solution to Problem

An RRI measurement device of embodiments of the present invention includes: a first detection unit configured to detect a peak point of an R wave from a sampling data sequence of an electrocardiogram signal of a subject; a second detection unit configured to estimate a waveform near the R wave of the electrocardiogram signal on the basis of the peak point of the R wave detected by the first detection unit and sampling data of the electrocardiogram signal before and after the peak point and to detect the peak point of the R wave again on the basis of the estimated waveform; and a calculation unit configured to calculate an RRI on the basis of time-series data of the peak point of the R wave detected by the second detection unit.

An RRI measurement method of embodiments of the present invention includes: a first step of detecting a peak point of an R wave from a sampling data sequence of an electrocardiogram signal of a subject; a second step of estimating a waveform near the R wave of the electrocardiogram signal on the basis of the peak point of the R wave detected in the first step and sampling data of the electrocardiogram signal before and after the peak point and detecting the peak point of the R wave again on the basis of the estimated waveform; and a third step of calculating an RRI from time-series data of the peak point of the R wave detected in the second step.

Further, an RRI measurement program of embodiments of the present invention causes a computer to execute each of the above steps.

Advantageous Effects of Embodiments of Invention

According to embodiments of the present invention, providing a first detection unit, a second detection unit, and a calculation unit makes it possible to accurately measure an RRI of a subject on the basis of sampling data of an electrocardiogram signal acquired at a low sampling rate. In embodiments of the present invention, it is unnecessary to acquire an electrocardiogram signal at a high sampling rate, and thus it is possible to reduce power consumption of an RRI measurement device.

DETAILED DESCRIPTION OF ILLUSTRATIVE EMBODIMENTS

Figure 1:
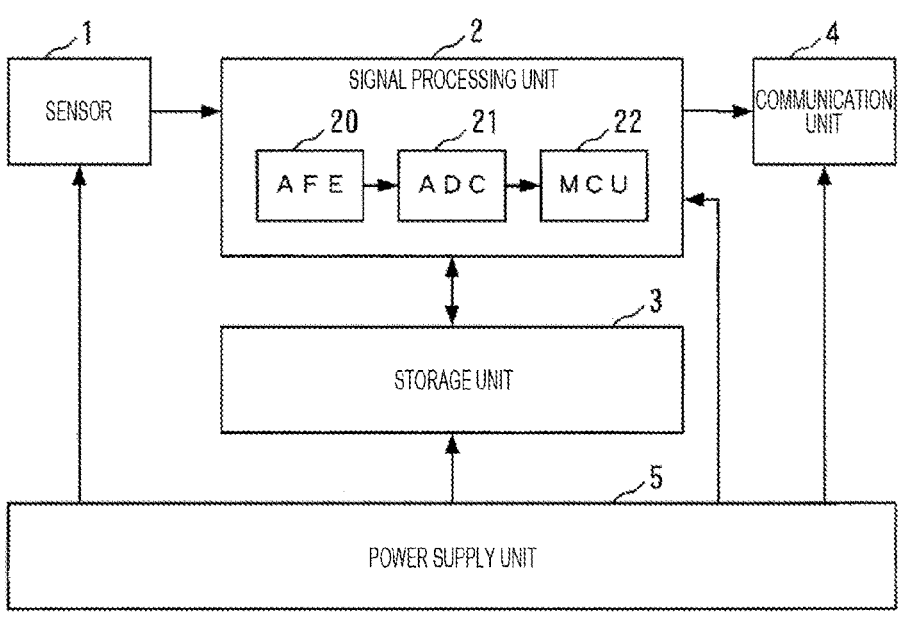
FIG. 1 is a block diagram showing a configuration of an RRI measurement device according to an embodiment of the present invention.

Hereinafter, an embodiment of the present invention will be described with reference to the drawings. FIG. 1 is a block diagram showing a configuration of an RRI measurement device according to an embodiment of the present invention. The RRI measurement device includes a sensor 1, a signal processing unit 2, a storage unit 3, a communication unit 4, and a power supply unit 5.

The signal processing unit 2 includes an analog front end (AFE) 20, an analog digital converter (ADC) 21, and a micro control unit (MCU) 22.

The sensor 1 detects an ECG signal of a subject. The AFE 20 amplifies a weak ECG signal detected by the sensor 1.

The ADC 21 converts the ECG signal amplified by the AFE 20 into digital data at a predetermined sampling rate. Examples of the sampling rate include 125 samples/sec. and 250 samples/sec.

Figure 2:
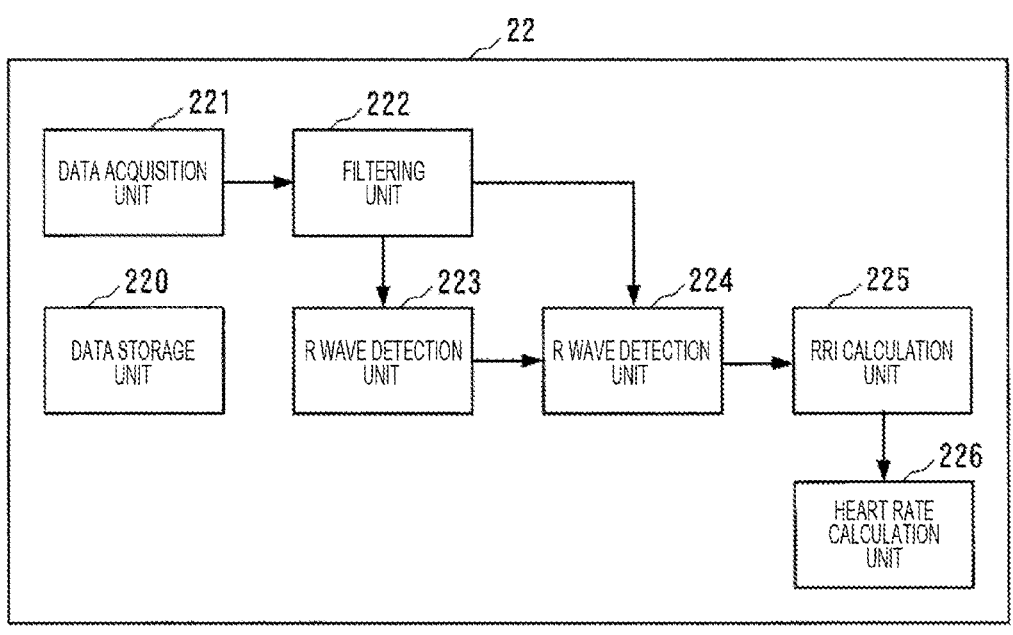
FIG. 2 is a functional block diagram of an MCU of an RRI measurement device according to an embodiment of the present invention.

The MCU 22 is a circuit that performs signal processing for calculating an RRI. FIG. 2 is a functional block diagram of the MCU 22. The MCU 22 functions as a data storage unit 220, a data acquisition unit 221, a filtering unit 222, an R wave detection unit 223 (first detection unit), an R wave detection unit 224 (second detection unit), an RRI calculation unit 225, and a heart rate calculation unit 226.

The storage unit 3 stores a program of the MCU 22, sampling data of an ECG signal output from the ADC 21, and data calculated by the MCU 22.

The data storage unit 220 of the MCU 22 adds sampling time information to each piece of sampling data of ECG signals output from the ADC 21 and stores the sampling data in the storage unit 3.

The communication unit 4 includes a circuit that wirelessly transmits the sampling data of the ECG signal and the data calculated by the MCU 22 to an external device (not illustrated) such as a smartphone.

The power supply unit 5 is a circuit that supplies power to the entire RRI measurement device.

Figure 3:
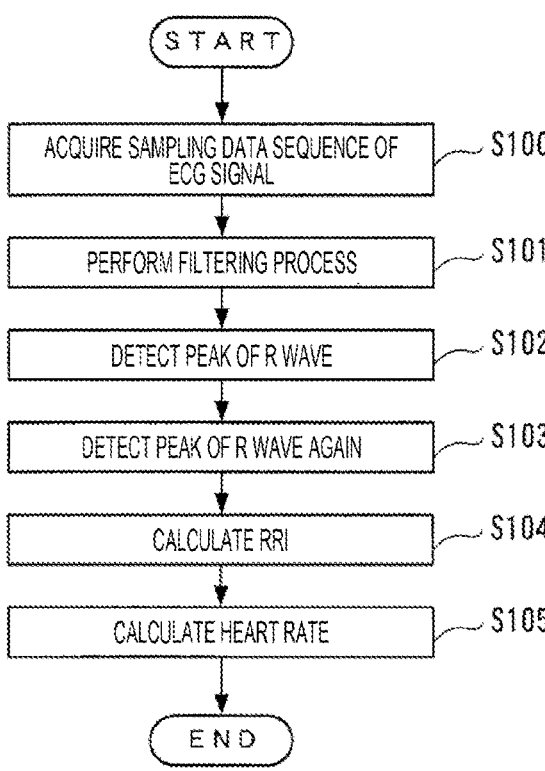
FIG. 3 is a flowchart showing an operation of an MCU of an RRI measurement device according to an embodiment of the present invention.

FIG. 3 is a flowchart showing an operation of the MCU 22. The data acquisition unit 221 acquires a sampling data sequence of an ECG signal stored in the storage unit 3 (step S100 in FIG. 3).

The filtering unit 222 performs a filtering process by using an anti-aliasing filter or band-pass filter on the sampling data sequence acquired by the data acquisition unit 221 (step S101 in FIG. 3).

The R wave detection unit 223 detects a peak point of an R wave from the sampling data sequence subjected to the filtering process (step S102 in FIG. 3). As a method of detecting the peak point of the R wave, a method using a threshold is simple. Specifically, the R wave detection unit 223 only needs to detect a section in which the sampling data exceeds a predetermined threshold as the R wave and set a point having the highest potential in the data exceeding the threshold as the peak point of the R wave.

The R wave detection unit 223 may detect the peak point of the R wave by another method. Another method is, for example, a method of using a time difference of an ECG signal. In the present embodiment, a value (potential) of the sampling data of the ECG signal is denoted by A(n), and a sampling time is denoted by T(n). The letter "n" is a number given to data of one sampling. It is needless to say that the sampling time is later as the number n is larger.

The R wave detection unit 223 calculates a time difference value Y(n) of the sampling data A(n) as in the following expression by using data A(n+1) one sampling after the sampling data A(n) and data A(n−1) one sampling therebefore.

$$Y(n)=A(n+1)-A(n-1) \tag{1}$$

Figure 4:
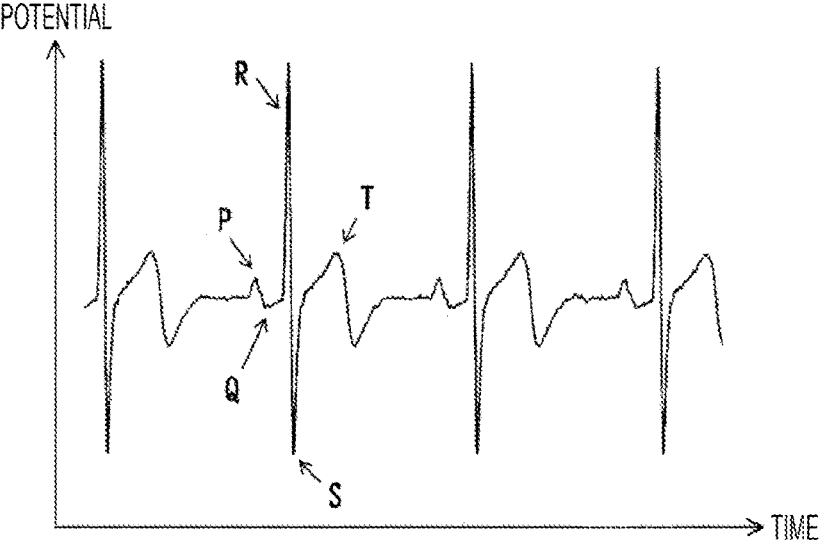
FIG. 4 is a waveform diagram showing an example of an ECG signal.

The R wave detection unit 223 calculates the time difference value Y(n) at each sampling time (each piece of the sampling data). As shown in FIG. 4, the ECG signal has a continuous heartbeat waveform, and one heartbeat waveform includes components such as a P wave, Q wave, R wave, S wave, and T wave each of which reflects activity of atria or ventricles. Therefore, for the time difference value Y(n), a peak caused by a steep change from the R wave to the S wave appears as a negative value. When detecting a negative peak point of the time difference value Y(n), the R wave detection unit 223 sets a positive peak point immediately before the negative peak point as a peak point of the R wave.

Next, the R wave detection unit 224 estimates a waveform near the R wave of the ECG signal on the basis of the peak point of the R wave detected by the R wave detection unit 223 and sampling data before and after the peak point and detects the peak point of the R wave again on the basis of the estimated waveform (step S103 in FIG. 3). Specifically, the R wave detection unit 224 obtains an approximate curve (quadratic curve) such as Expression (2) matching with three points, i.e., the peak point of the R wave and the sampling data of the ECG signal before and after the peak point, and sets a peak of the approximate curve as the peak of the R wave.

$$A=aT^2+bT+c \tag{2}$$

A potential at the peak point of the R wave detected by the R wave detection unit 223 is denoted by A[n], a time thereof is denoted by T[n], a potential at a sampling point m point(s) before the peak point is denoted by A[n−m], a time thereof is denoted by T[n−m]=T[n]−mΔt (Δt denotes a sampling period), a potential at a sampling point m* point(s) after the peak point is denoted by A[n+m*], and a time thereof is denoted by T[n+m*]=T[n]+m*Δt. The R wave detection unit 224 calculates coefficients a, b, and c of an approximate curve matching with the peak point of the R wave, the sampling point m point(s) before the peak point, and the sampling point m* point(s) after the peak point as in the following expression.

Equation 1

$$\begin{pmatrix} a \\ b \\ c \end{pmatrix} = \begin{pmatrix} (T[n-m])^2 & T[n-m] & 1 \\ (T[n])^2 & T[n] & 1 \\ (T[n+m^*])^2 & T[n+m^*] & 1 \end{pmatrix}^{-1} \begin{pmatrix} A[n-m] \\ A[n] \\ A[n+m^*] \end{pmatrix} \tag{3}$$

Figure 5A:
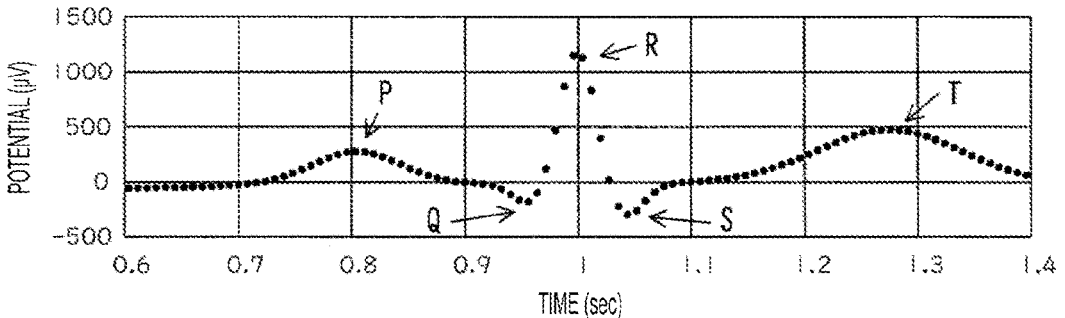
FIGS. 5A and 5B are explanatory diagrams showing processing of an R wave detection unit of an RRI measurement device according to an embodiment of the present invention.
Figure 5B:
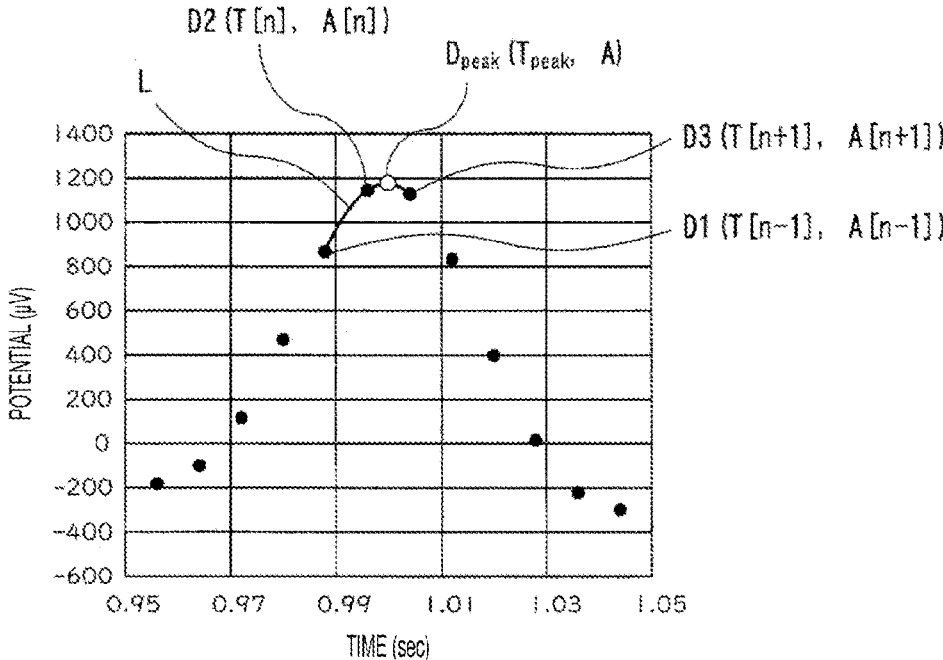

FIGS. 5A and 5B are explanatory diagrams showing processing of the R wave detection unit 224. FIG. 5A shows an example of the sampling data sequence of the ECG signal, and FIG. 5B is an enlarged view of a section from 0.95 seconds to 1.05 seconds in FIG. 5A. FIGS. 5A and 5B show an example where m=m*=1 is established and an approximate curve matching with the peak point of the R wave and the sampling points immediately before and immediately after the peak point is obtained. D2 in FIG. 5B is the peak point of the R wave detected by the R wave detection unit 223, D1 is the sampling point immediately before the peak point D2, and D3 is a sampling point immediately after the peak point D2. An approximate curve L can be expressed by Expression (2).

When the coefficients a, b, and c of the approximate curve L are obtained, a peak point $D_{peak}$ of the approximate curve L is determined. A time of the peak point $D_{peak}$ is shifted by $-b/2a$ from the time T[n] of the peak point D2 of the R wave detected by the R wave detection unit 223. Therefore, the R wave detection unit 224 calculates the time of the peak point $D_{peak}$ as a time $T_{peak}$ of the peak point of the R wave.

$$T_{peak}=T[n]-b/2a \qquad (4)$$

The R wave detection unit 224 performs the above processing at each peak point of the R wave detected by the R wave detection unit 223. The time $T_{peak}$ of the peak point $D_{peak}$ of the R wave and time-series data of the potential A are stored in the storage unit 3. Note that the peak point of the approximate curve may be calculated by another method.

Next, the RRI calculation unit 225 calculates a time interval between two adjacent times $T_{peak}$ as an RRI from the time-series data of the times $T_{peak}$ of the peak points $D_{peak}$ of the R waves stored in the storage unit 3 (step S104 in FIG. 3). The RRI calculation unit 225 calculates the RRI for each peak point $D_{peak}$. Time-series data of the calculated RRIs is stored in the storage unit 3. The RRI calculation unit 225 may calculate not only the RRIs but also an average value of the RRIs.

The heart rate calculation unit 226 calculates an instantaneous heart rate X (beats/min.) for each RRI on the basis of the RRIs calculated by the RRI calculation unit 225 (step S105 in FIG. 3).

$$X=60000/RRI \qquad (5)$$

Time-series data of the calculated instantaneous heart rate X is stored in the storage unit 3. The heart rate calculation unit 226 may calculate not only the instantaneous heart rate X but also an average value of the instantaneous heart rate X.

The communication unit 4 wirelessly transmits the sampling data sequence of the ECG signal, the time-series data of the RRIs and the average value of the RRIs calculated by the RRI calculation unit 225, and the time-series data of the instantaneous heart rate X and the average value of the instantaneous heart rate X calculated by the heart rate calculation unit 226 to the external device such as a smartphone.

Therefore, in the present embodiment, it is possible to accurately measure the RRIs and the heart rate of the subject on the basis of the sampling data of the ECG signal acquired at a low sampling rate such as 125 samples/sec. or 250 samples/sec. In the present embodiment, it is unnecessary to acquire the ECG signal at a sampling rate higher than 500 samples/sec., and thus it is possible to reduce power consumption of the RRI measurement device.

In the present embodiment, the peak of the R wave is detected after the sampling data sequence of the ECG signal is subjected to the filtering process, but the filtering unit 222 is not an essential component in the present invention.

Figure 6:
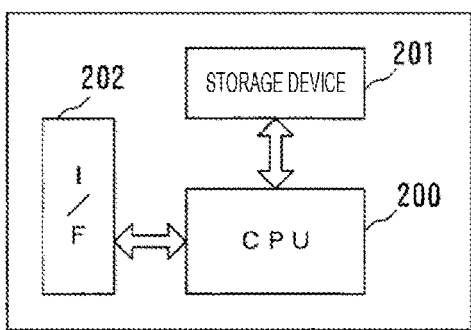
FIG. 6 is a block diagram showing a configuration example of a computer that implements an RRI measurement device according to an embodiment of the present invention.

The storage unit 3 and the MCU 22 described in the present embodiment can be implemented by a computer including a central processing unit (CPU), a storage device, and an interface and a program for controlling those hardware resources. A configuration example of the computer is illustrated in FIG. 6. The computer includes a CPU 200, a storage device 201, and an interface device (hereinafter, abbreviated as the I/F) 202. The I/F 202 is connected to the ADC 21, the communication unit 4, and the like. In such a computer, an RRI measurement program for implementing the RRI measurement method of embodiments of the present invention is stored in the storage device 201. The CPU 200 executes the processing described in the present embodiment according to the program stored in the storage device 201. The program can also be provided via a network.

INDUSTRIAL APPLICABILITY

Embodiments of the present invention can be applied to a technique for measuring an RRI.

REFERENCE SIGNS LIST

1 Sensor
2 Signal processing unit
3 Storage unit
4 Communication unit
5 Power supply unit
20 AFE
21 ADC
22 MCU
220 Data storage unit
221 Data acquisition unit
222 Filtering unit
223, 224 R wave detection unit
225 RRI calculation unit
226 Heart rate calculation unit.

The invention claimed is:

1. An RRI measurement device comprising:
a first detection circuit configured to detect a peak point of an R wave from a sampling data sequence of an electrocardiogram signal of a subject;
a second detection circuit configured to:
estimate a waveform within a predetermined range of the R wave of the electrocardiogram signal based on the peak point of the R wave detected by the first detection circuit and sampling data of the electrocardiogram signal before and after the peak point; and
detect the peak point of the R wave again based on the estimated waveform; and
a calculation circuit configured to calculate an RRI based time-series data of a time Tpeak of the peak point of the R wave detected by the second detection circuit,
wherein the first detection circuit is configured to calculate time difference values for respective sampling data from the sampling data sequence of the electrocardiogram signal and detect a positive peak point of the time difference values immediately before a negative peak point of the time difference values, and set the detected positive peak point as the peak point of the R wave.

2. The RRI measurement device according to claim 1, wherein:
the second detection circuit is configured to obtain an approximate curve matching with three points and set a peak of the approximate curve as the peak of the R wave, wherein the three points are the peak point of the R wave detected by the first detection circuit and sampling points of the electrocardiogram signal before and after the peak point.

3. The RRI measurement device according to claim 2, wherein:
the second detection circuit is configured to calculate coefficients a, b, and c of the approximate curve expressed by a following expression (1):

$$A=aT^2+bT+c \qquad (1)$$

where a value of the sampling data of the electrocardiogram signal is denoted by "A", and a sampling time is denoted by "T", wherein the second detection circuit is configured to calculate a time of a peak point of the expression (1) as the time $T_{peak}$ of the peak point of the R wave on the basis of a time T[n] of the peak point of the R wave detected by the first detection circuit and the coefficients a and b, and wherein the time of the peak point of the expression (1) is expressed by a following expression (2):

$$T_{peak}=T[n]-b/2a \tag{2}$$

4. The RRI measurement device according to claim 1, further comprising:

a filtering circuit provided in a preceding stage of the first detection circuit and the second detection circuit, the filtering circuit configured to perform an anti-aliasing filtering process or band-pass filtering process on the sampling data sequence of the electrocardiogram signal, wherein the first detection circuit and the second detection circuit are each configured to detect the peak point of the R wave using the sampling data sequence processed by the filtering circuit.

5. The RRI measurement device according to claim 1, wherein:

the RRI measurement device further comprising an Analog Digital Converter acquiring the electrocardiogram signal in real-time.

6. The RRI measurement device according to claim 5, wherein:

the Analog Digital Converter converts the electrocardiogram signal into digital data at a sampling rate of at least 125 samples/sec.

7. An RRI measurement method comprising:

a first step of detecting a peak point of an R wave from a sampling data sequence of an electrocardiogram signal of a subject;

a second step of estimating a waveform within a predetermined range of the R wave of the electrocardiogram signal based on the peak point of the R wave detected in the first step and sampling data of the electrocardiogram signal before and after the peak point and detecting the peak point of the R wave again on the basis of the estimated waveform; and a third step of calculating an RRI from time-series data of a time Tpeak of the peak point of the R wave detected in the second step, wherein the first step comprising calculating time difference values for respective sampling data from the sampling data sequence of the electrocardiogram signal, detecting a positive peak point of the time difference values immediately before a negative peak point of the time difference values, and setting the detected positive peak point as the peak point of the R wave.

8. The RRI measurement method according to claim 7, wherein the second step comprises obtaining an approximate curve matching with three points and setting a peak of the approximate curve as the peak of the R wave, wherein the three points are the peak point of the R wave detected in the first step and sampling points of the electrocardiogram signal before and after the peak point.

9. The RRI measurement method according to claim 8, wherein:

the second step comprises calculating coefficients a, b, and c of the approximate curve expressed by a following expression (1):

$$A=aT^2+bT+c \tag{1}$$

where a value of the sampling data of the electrocardiogram signal is denoted by "A", and a sampling time is denoted by "T", wherein a time of a peak point of the above expression (1) is calculated as the time $T_{peak}$ of the peak point of the R wave on the basis of a time T[n] of the peak point of the R wave detected in the first step and the coefficients a and b, and wherein the time of the peak point of the expression (1) is expressed by a following expression (2):

$$T_{peak}=T[n]-b/2a \tag{2}$$

10. The RRI measurement method according to claim 7, further comprising:

a fourth step of performing, by a filtering circuit, an anti-aliasing filtering process or band-pass filtering process on the sampling data sequence of the electrocardiogram signal prior to the first step, wherein the first step and the second step comprise detecting the peak point of the R wave using the sampling data sequence processed by the filtering circuit.

11. The RRI measurement method according to claim 7, wherein:

the method further comprising a step of acquiring the electrocardiogram signal in real-time.

12. The RRI measurement method according to claim 11, wherein:

the method further comprising a step of converting the electrocardiogram signal into digital data at a sampling rate of at least 125 samples/sec.

13. A non-transitory computer readable storage medium storing an RRI measurement program for causing a computer to execute a method comprising:

a first step of detecting a peak point of an R wave from a sampling data sequence of an electrocardiogram signal of a subject;

a second step of estimating a waveform within a predetermined range of the R wave of the electrocardiogram signal based on the peak point of the R wave detected in the first step and sampling data of the electrocardiogram signal before and after the peak point and detecting the peak point of the R wave again on the basis of the estimated waveform; and a third step of calculating an RRI from time-series data of a time Tpeak of the peak point of the R wave detected in the second step, wherein the first step comprises calculating time difference values for respective sampling data from the sampling data sequence of the electrocardiogram signal, detecting a positive peak point of the time difference values immediately before a negative peak point of the time difference values, and setting the detected positive peak point as the peak point of the R wave.

14. The non-transitory computer readable storage medium according to claim 13, wherein:

a second detection step comprises obtaining an approximate curve matching with three points and setting a peak of the approximate curve as the peak of the R wave, wherein the three points are the peak point of the R wave detected by a first detection circuit and sampling points of the electrocardiogram signal before and after the peak point.

15. The non-transitory computer readable storage medium according to claim 14, wherein:

the second step comprises calculating coefficients a, b, and c of the approximate curve expressed by a following expression (1):

$$A=aT^2+bT+c \tag{1}$$

where a value of the sampling data of the electrocardiogram signal is denoted by "A", and a sampling time is denoted by "T", wherein a time of a peak point of the expression (1) is calculated as the time $T_{peak}$ of the peak point of the R wave on the basis of a time T[n] of the peak point of the R wave detected in the first step and the coefficients a and b, and wherein the time of the peak point of the expression (1) is expressed by a following expression (2):

$$T_{peak}=T[n]-b/2a \tag{2}$$

16. The non-transitory computer readable storage medium according to claim 13, wherein:

the method further comprising a step of acquiring the electrocardiogram signal in real-time.

17. The non-transitory computer readable storage medium according to claim 16, wherein:

the method further comprising a step of converting the electrocardiogram signal into digital data at a sampling rate of at least 125 samples/sec.

* * * * *